(12) United States Patent
Coombs

(10) Patent No.: US 10,197,494 B2
(45) Date of Patent: Feb. 5, 2019

(54) FLOW CELL AND SYSTEM FOR SIMULTANEOUS MEASUREMENT OF ABSORBANCE AND EMISSION IN A SAMPLE

(71) Applicant: BioComp Instruments Inc., Fredericton (CA)

(72) Inventor: David Coombs, Fredericton (CA)

(73) Assignee: Biocomp Instruments Inc., Fredericton, NB (CA)

( * ) Notice: Subject to any disclaimer, the term of this patent is extended or adjusted under 35 U.S.C. 154(b) by 0 days.

(21) Appl. No.: 15/631,618

(22) Filed: Jun. 23, 2017

(65) Prior Publication Data

US 2017/0370826 A1     Dec. 28, 2017

Related U.S. Application Data

(60) Provisional application No. 62/353,783, filed on Jun. 23, 2016.

(51) Int. Cl.
*G01N 21/05* (2006.01)
*G01N 21/03* (2006.01)
(Continued)

(52) U.S. Cl.
CPC ......... *G01N 21/05* (2013.01); *G01N 21/0303* (2013.01); *G01N 2021/0193* (2013.01);
(Continued)

(58) Field of Classification Search
CPC ........ G01N 21/05; G01N 21/03; G01N 21/01; G01N 21/0303; G01N 2021/0193
See application file for complete search history.

(56) References Cited

U.S. PATENT DOCUMENTS 3,151,204 A * 9/1964 Stacy ................. G01N 21/6445
                                                    250/225
3,573,470 A * 4/1971 Haley .................... G01N 21/05
                                                    250/239

(Continued)

*Primary Examiner* — Sang H Nguyen
(74) *Attorney, Agent, or Firm* — Gowling WLG (Canada) LLP

(57) ABSTRACT

The flow cell of the present application simultaneously monitors and measures light absorbance and fluorescence of particles in a flowing liquid. The flow cell comprises a housing having a light input face, an absorbance output face and first and second emission output faces; a fluid flow section within the housing that comprises a bottom funnel through which fluid enters the flow cell, a core chamber into which fluid flows from the bottom funnel, and a top funnel into which fluid flows from the core chamber, wherein the bottom and top funnels each comprise a first end which extends at an angle to a second end that is wider in diameter than the first end, and said second end of each is adjacent to and aligned with the core chamber; and a center section within the housing center having a recess formed therein which houses the core chamber of the fluid flow section, wherein said center section comprises a first pair of opposing channels formed in the light input face and the absorbance output face, respectively, and a second pair of opposing channels formed in the first emission output face and the second emission output face and which are perpendicular to the first pair of opposing channels, and wherein the first pair of opposing channels and second pair of opposing channels are in communication with the core chamber. An apparatus comprising the flow cell is also provided.

18 Claims, 14 Drawing Sheets

(51) Int. Cl.
*G01N 21/01* (2006.01)
*G01N 21/64* (2006.01)

(52) U.S. Cl.
CPC ............... *G01N 2021/6482* (2013.01); *G01N 2201/0627* (2013.01); *G01N 2201/0806* (2013.01)

(56) References Cited

U.S. PATENT DOCUMENTS

| | | | |
|---|---|---|---|
| 3,728,032 A | 4/1973 | Noll | |
| 3,920,334 A | 11/1975 | Steichen et al. | |
| 4,008,397 A | 2/1977 | Zdrodowski | |
| 4,076,420 A * | 2/1978 | De Maeyer | G01N 21/253 |
| | | | 356/246 |
| 4,180,739 A | 12/1979 | Abu-Shumays | |
| 4,181,853 A | 1/1980 | Abu-Shumays et al. | |
| 4,260,257 A | 4/1981 | Neeley et al. | |
| 4,834,534 A | 5/1989 | Wiget | |
| 5,034,194 A | 7/1991 | Miller et al. | |
| 5,125,737 A * | 6/1992 | Rodriguez | G01N 15/1459 |
| | | | 356/338 |
| 5,371,585 A * | 12/1994 | Morgan | G01N 15/1404 |
| | | | 356/246 |
| 5,430,541 A | 7/1995 | Sapp et al. | |
| 5,734,468 A * | 3/1998 | McNeal | B01L 3/021 |
| | | | 356/244 |
| 6,388,746 B1 | 5/2002 | Eriksson et al. | |
| 8,241,570 B1 | 8/2012 | Shen et al. | |
| 8,248,604 B2 | 8/2012 | Takeda | |
| 8,649,005 B2 | 2/2014 | Tormod | |
| 8,767,212 B2 | 7/2014 | Kanda et al. | |
| 8,951,474 B2 | 2/2015 | Takeda | |
| 8,975,572 B2 | 3/2015 | Hargis | |
| 9,222,876 B2 | 12/2015 | Bartlett et al. | |
| 9,267,887 B2 | 2/2016 | Kanomata et al. | |
| 9,500,591 B1 * | 11/2016 | Goad | G01N 21/6486 |
| 2008/0223154 A1 * | 9/2008 | Kondo | G01N 15/1404 |
| | | | 73/865.5 |
| 2009/0012721 A1 * | 1/2009 | Kimura | G01N 21/274 |
| | | | 702/23 |
| 2010/0290041 A1 * | 11/2010 | Graham | C03B 23/04 |
| | | | 356/246 |
| 2012/0307241 A1 * | 12/2012 | Maity | G01J 3/02 |
| | | | 356/326 |
| 2014/0099659 A1 * | 4/2014 | Keller | G01N 21/6486 |
| | | | 435/29 |
| 2016/0011098 A1 * | 1/2016 | Graham | C03B 23/047 |
| | | | 356/246 |

* cited by examiner

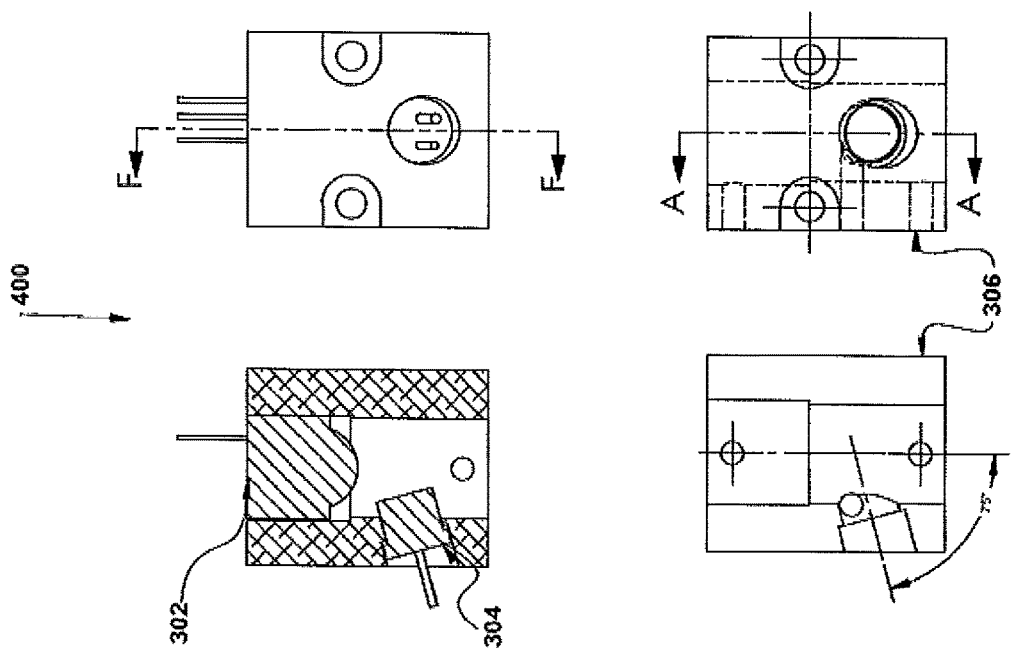

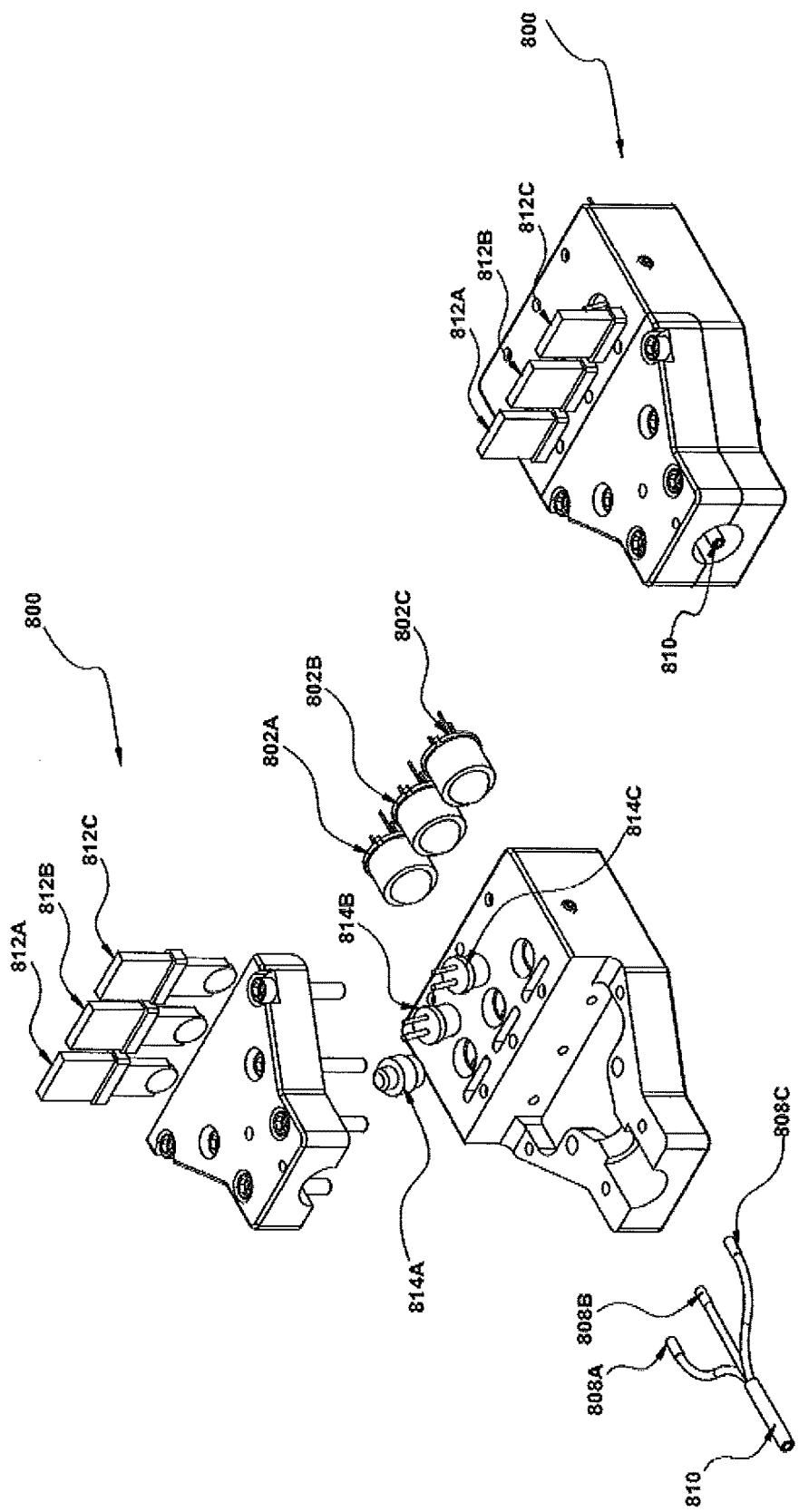

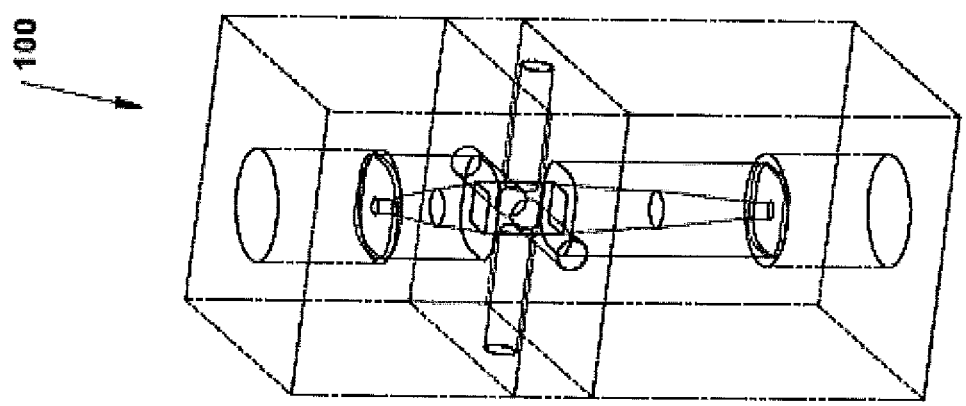
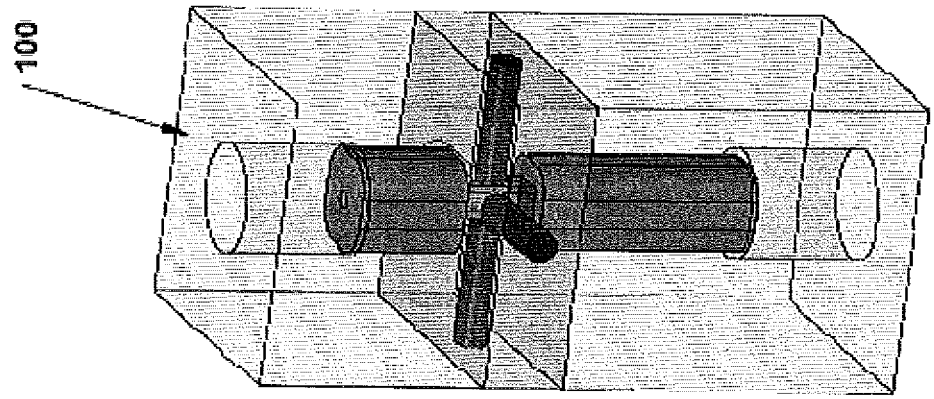
Figure 9

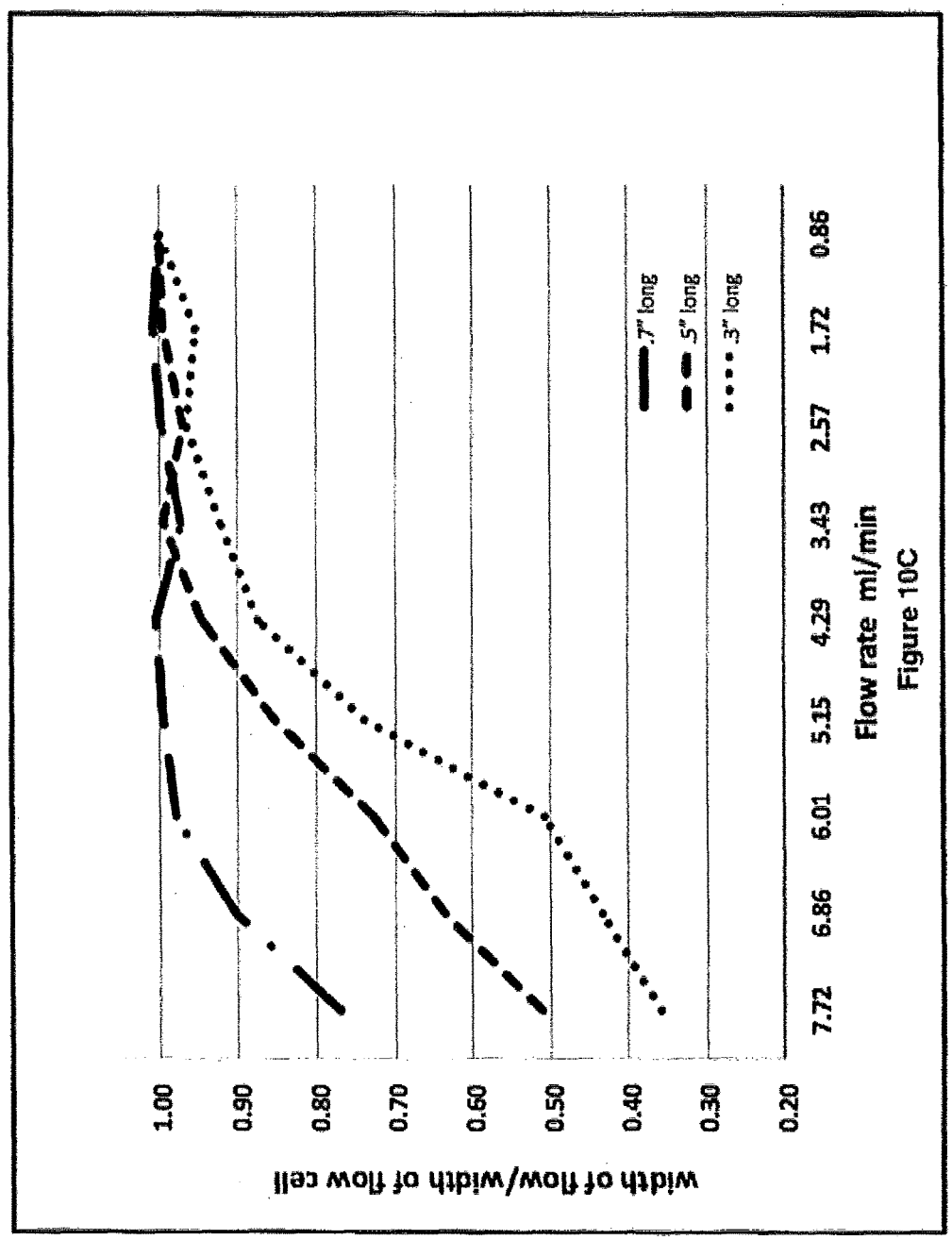

FLOW CELL AND SYSTEM FOR SIMULTANEOUS MEASUREMENT OF ABSORBANCE AND EMISSION IN A SAMPLE

FIELD OF THE INVENTION

The present application relates to an apparatus for monitoring particles in a flowing liquid. In particular, the present application relates to a flow cell and apparatus for monitoring and measuring the absorbance and fluorescence of particles in a flowing liquid.

BACKGROUND OF THE INVENTION

Chromatographic and density gradient separation of particles are utilized in biochemical research to separate macromolecules such as proteins, DNA and RNA, and larger aggregates such as enzyme complexes, ribosomes, viruses and cells. With such applications, it may be necessary to monitor the absorbance and fluorescence of particles within a flowing liquid sample, typically within a flow cell. Ultraviolet-visible spectroscopy (UV-Vis or UV/Vis) refers to absorption spectroscopy or reflectance spectroscopy in the ultraviolet-visible spectral region, where absorption measures transitions from the ground state to the excited state. Fluorescence spectroscopy deals with transitions from an excited state to a ground state.

Conventional methods and apparatuses provide monitoring of the absorbance of particles in a flowing liquid. For example, one conventional flow cell (U.S. Pat. No. 8,649,005) provides an optical flow cell detector comprising a sample inlet and outlet in fluidic communication through a flow cell channel of cross sectional area A, an input light guide with a light exit surface arranged adjacent and in optical alignment with a light entrance surface of an output light guide. The input light guide and the output light guide protrude into the flow cell channel. The distance between the light exit surface and the light entrance surface is less than 1.0 mm, and the cross sectional area of the protruding portions of the input light guide and the output light guide in the flow direction is less than A/2.

As well, conventional methods and apparatuses provide monitoring of the fluorescence of particles in a flowing liquid. For example, one conventional flow cell assembly (U.S. Pat. No. 9,267,887) includes a high-pressure flow cell having a cell body made of a light-transmissive material, wherein the cell body is penetrated by a straight-line flow path for a high-pressure fluid, which allows the high-pressure fluid to be irradiated with excitation light and allows fluorescence of the high-pressure fluid to be detected.

However, neither of these flow cell designs are of use where separation of particles of interest is the goal, as it is in chromatography (e.g. FPLC and HPLC) and density gradient centrifugation. In the flow cell of U.S. Pat. No. 8,649,005, the protruding light guides may give variable path length, but they also disrupt the smooth flow of the liquid moving around them and through the gap between them. If the input liquid represents a stream of particles separated from each other by some means, the resultant turbulence, the comparatively large volume of the flow cell and the large surface area of its threaded light probes will produce smearing of the flowing liquid and a resultant loss of resolution. Additionally, this design is incompatible with fluorescence detection where a large volume of sample needs to be queried to produce a reasonable fluorescence signal.

In addition, the example fluorescence flow cells discussed above are unable to measure absorbance.

One conventional flow cell design described in U.S. Pat. No. 3,728,032 provides an oval cross section at its center, and tall, elliptical windows for optical measurements at the apices of the oval. The overall shape is one of a flattened elongated bubble having a long X-axis in the direction of the absorption light path and a much shorter Y-axis dimension. With the flow cell in U.S. Pat. No. 3,728,032, the readings are sampling an asymmetrical elongated area of a flow path. As well, the flow cell of U.S. Pat. No. 3,728,032 cannot measure fluorescence.

Another conventional flow cell design is described in U.S. Pat. No. 3,920,334 which may measure absorbance and fluorescence in applications other than density gradients. Particularly, this design views the liquid flow from outside a round glass tubing that contains the flow, which may result in a large loss of light that is compensated for with a fluorescent reflector. As well, the volume of liquid from which fluorescence and absorption signals are measured is very large, resulting in a low resolution in the flow cell which is not suitable for density gradient applications.

The only commercially available flow cell capable of both fluorescence and absorption is the PRO–FC–FL+TR (Ocean Optics, Dunedin, Fla.). However, it is designed for industrial online flow analysis applications, not for low volume separation technologies. Its adjustable path length (0.5-15 mm) indicates that it has the same disruptive interior design as the flow cell of U.S. Pat. No. 8,649,005, making it unsuitable for use with, for example, separation technologies.

One can describe three basic categories of flow cells: 1) large flow rate cells used in process technologies such as chemical production, 2) small flow rate cells like the analytical fluorescence example above, where the digital/graphic output from the flow cell is the desired result, and 3) small flow analytical cells in which the flow cell's output is informative, but the species of different particles identified in the graphic trace are processed in some way downstream of the flow cell. There is a key difference between the latter two analytical application flow cells. In the third type, the resolution achieved by the separation method (that is the source of the flow), i.e. centrifugation or chromatography, depends on fluid flow through the flow cell with as little disturbance and mixing as possible.

It would be desirable to develop an improved analytical flow cell which provides improved resolution and/or flexibility with respect to measuring light absorbance and/or emission (e.g. fluorescence).

SUMMARY OF THE INVENTION

A flow cell has now been developed that provides both low flow and low disturbance. For example, a flow cell in accordance with embodiments of the invention 1) manages flow rates in the range of 0.5-7.0 ml/min, 2) has a geometry which minimizes mixing and turbulence, preserving the resolution achieved in the flow's source, 3) allows simultaneous measurement of both absorbance and fluorescence in the flowing liquid, 4) can simultaneously measure absorbance and/or fluorescence at multiple wavelengths in the UV-IR (200-1200 nm) spectrum, 5) has a modular design allowing the user to tailor the flow cell's capabilities to meet their needs, and/or 6) uses a suitable electronic means to display, record, save and manipulate multiple digital data streams that the device will generate during a scan.

The flow cell in accordance with embodiments of the present application includes: 1) a tapered flow path, reducing turbulence to limit chaotic mixing and noise; 2) sampling of absorbance by a straight light path from the light source to absorbance photodiode; 3) sampling of fluorescence at right angles to the absorbance light path, 4) dual fluorescence measurements; 5) a square cross section in the flow path to permit both fluorescent and absorbance measurements simultaneously, and/or 6) limited height of the flow path (the Z axis) to maximize the resolution provided by the flow cell given its dual functionality.

Thus, in one embodiment, a flow cell is provided comprising:
a housing having four faces, a light input face opposed to an absorbance output face, and a first emission output face opposed to a second emission output face;
a fluid flow section within the housing that comprises a bottom funnel through which fluid enters the flow cell, a core chamber into which fluid flows from the bottom funnel, and a top funnel into which fluid flows from the core chamber, wherein the bottom and top funnels each comprise a first end which extends at an angle to a second end that is wider in diameter than the first end, and said second end of each is adjacent to and aligned with the core chamber; and
a center section within the housing having a recess formed therein which houses the core chamber of the fluid flow section, wherein said center section comprises a first pair of opposing channels formed in the light input face and the absorbance output face, respectively, and a second pair of opposing channels formed in the first emission output face and the second emission output face and which are perpendicular to the first pair of opposing channels, and wherein the first pair of opposing channels and second pair of opposing channels are in communication with the recess in the center section.

In another embodiment, a flow cell apparatus comprising the flow cell is provided. The apparatus additionally comprises:
one or more light sources at the light input face of the flow cell housing for directing light into liquid in the core chamber of the flow cell;
one or more absorbance photodiodes at the absorbance output face of the flow cell housing for measuring light absorbance within the liquid in the core chamber of the flow cell; and
fluorescence photodiodes at each of the first and second emission output faces of the flow cell housing for measuring fluorescence within liquid in the core chamber of the flow cell.

BRIEF DESCRIPTION OF THE DRAWINGS

Embodiments of the invention are described below with reference to the following drawings:

FIG. 4 is a plan view of a single input LED/PD holder, according to an embodiment of the present application;

FIG. 8A is an exploded view of a three input module for use with the flow cell of FIG. 1, according to a third embodiment of the present application;

FIG. 8B is a perspective view of an assembled three input module for use with the flow cell of FIG. 1, according to a third embodiment of the present application;

FIG. 9 is perspective views of the flow cell of FIG. 1, according to an embodiment of the present application;

FIG. 10C is a graph summarizing the flow characteristics of different lengths of funnels at different flow rates.

DETAILED DESCRIPTION OF THE INVENTION

Figure 1:
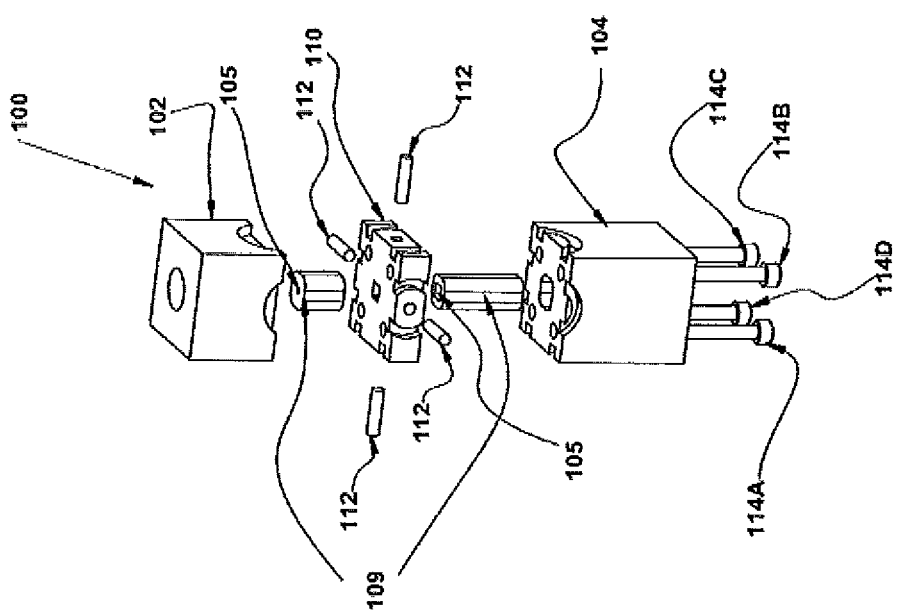
FIG. 1 is an exploded view of a flow cell according to an embodiment of the present application.

A flow cell 100 is provided as shown in FIG. 1 comprising a body top 102, a body bottom 104 and a center section 110 in the middle of the flow cell 100 between the body top 102 and body bottom 104. The body top 102 and the body bottom 104 form a square or rectangular external housing of the flow cell 100 for containing the internal components of the flow cell 100, including the fluid flow section 109. The flow cell center section 110 in some embodiments is made from an engineered thermoplastic such as polyoxymethylene (POM or Delrin) or stainless steel. The caustic cleaning solutions used with these flow cells rule out the use of aluminum or anodized aluminum. The flow cell 100 further comprises four suitable light pipes 112, i.e. devices having the appropriate physical and optical properties to transport light from a given light source, or to detect absorbed or emitted light, e.g. such as emitted fluorescence, for example, 1.5 mm ∅ fused silica rods. The light pipes 112 are received into four channels 101 (FIG. 2) formed in each external side of the flow cell center section 110. In some embodiments, the light pipes 112 comprise or communicate with a light source, e.g. an LED UV or visible light source, or photodetectors such as photodiodes to measure absorbed light and emitted fluorescent light, respectively. Generally, a light source light pipe is situated in an input face of the flow cell 100, a light pipe for a photodiode that measures absorbed light is situated in an absorbance output face of the flow cell 100 opposing the input face, and light pipes for photodiodes to measure fluorescence are situated on opposing emission output faces of the flow cell 100 which are at right angles to the input and absorbance output faces.

The light pipes 112 may be of different shapes. For example, in one embodiment they may be cylindrical with a circular cross-section. Since a square has a 27% greater surface area than a circle of the same size, should the need for more light become critical, in another embodiment, the light pipes 112 may have a rectangular rod shape having a square cross-section. Given the difficulty of machining or molding a square hole to accommodate these rectangular rods, in such an embodiment, the flow cell center section 110 may be split in half horizontally and square half recesses may be formed into each opposing face for the rectangular rod light pipes.

Figure 2:
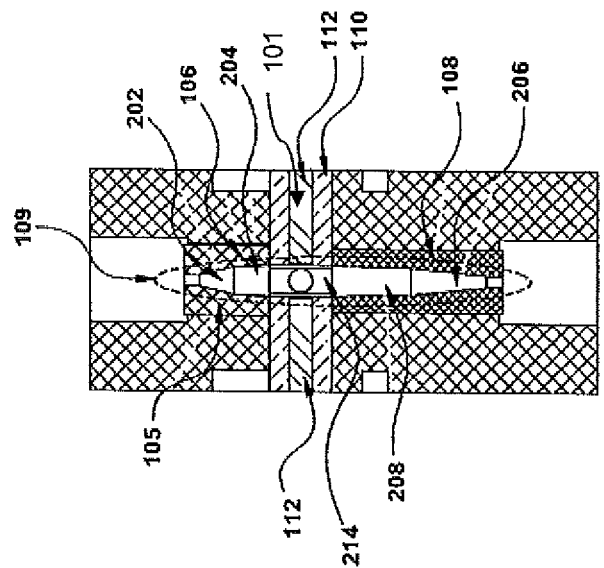
FIG. 2 is a central cross-section of the flow cell of FIG. 1, according to an embodiment of the present application.

The fluid flow section 109 of the flow cell 100 comprises a fluid path 105 that includes a bottom funnel 108 for fluid inflow, a central core chamber 214, and a top funnel 106 for fluid outflow as shown in FIG. 2. In some embodiments, the top funnel 106 and the bottom funnel 108 are molded from a plastic material, such as an engineered thermoplastic (e.g. polypropylene). The flow cell center section 110 is secured between the top funnel 106 and the bottom funnel 108. In one embodiment, a plurality of screws 114A-D (e.g. four) are used to secure the flow cell center section 110 with respect to the top and bottom funnels 106, 108. This modular assembly enables the flow cell to be dismantled for inspection and cleaning. Sealing of the liquid path is obtained by tightening tubing connectors (303A and 303B as shown in FIG. 3A) inserted into parts 102 and 104, forcing the flat-faced top and bottom funnels (106 and 108) against the central core (110).

As shown in FIG. 2, the bottom funnel 108 has a cone portion 206 and a cone-to-square conversion portion 208. Similarly, the top funnel 106 has a cone portion 202 and a cone-to-square conversion portion 204. The cone-to-square conversion portions 204 and 208 of the top and bottom funnels are aligned with central core chamber 214 to form the fluid path 105, giving a seamless, smooth transition from tubing to flow cell and back to tubing. The tapering of the bottom funnel 108 and the top funnel 106 by the cone portions 206 and 202, and cone-to-square conversion portions 208 and 204 keeps the flow of the liquid against the wall of the core chamber 214 as the liquid flows through the fluid path 105 of the fluid flow section 109 from bottom funnel 108 to the top funnel 106. The core chamber 214 is encased in a light-opaque, typically black, material of the central section 110. The central section has channels to receive the light pipes 112, e.g. the light pipe to transmit the input light into the core chamber 214, and light pipes 112 permitting light to travel out to the absorbance and fluorescence photodiodes for measuring absorbance and fluorescence, respectively, as shown in FIG. 3C. Liquid enters the vertical flow cell at the bottom cone portion 206, flows upwardly in the fluid path 105 of the fluid flow section 109 and exits at the top cone portion 202 of the fluid flow section 109. Since one application involves liquid flowing from a liquid density gradient, the vertical path can help suppress laminar capillary flow because of the inherent stability of the ever-increasing density of the flowing liquid. If the flow is in the opposite direction, top to bottom, or the flow cell is horizontal, this stability would be lost and the flow would be more chaotic and turbulent.

More particularly, the funnel design of the fluid path 105 of the flow cell 100 of the present application provides an input and an output of fluid that gradually spreads the liquid flow to cover the entire width of the core chamber 214 of the fluid flow section 109 of the flow cell 100. For example, due to the square cross section of the core chamber 214, the use of the cone-to-square conversion portions 204 and 208 facilitate a non-turbulent flow for monitoring a density gradient effluent. As well, with the square cross section of the core chamber 214, the fluid path 105 of the flow cell 100 is symmetrical in both the X-axis in the direction of the absorption light path and the Y-axis in the direction fluorescence light path. Accordingly, with the square cross section of the core chamber 214, the flow cell 100 provides sufficient light paths in both X and Y directions for simultaneous absorbance and fluorescent readings.

The light coverage of the Z axis (the direction of the flow, 315 as shown in FIG. 3C), is a matter of compromise between resolution and signal strength. The highest resolution requires the shortest possible Z-axis path, essentially a thin, horizontal blade of light, while the highest signal strength is obtained with a tall vertical light path. In practice, the Z-axis dimension of the light path can be tailored to meet the demands of the application. In density gradient work, for example, the ultra high resolution of the blade light path is unnecessary. If the blade is 0.1 mm tall by 2 mm wide, the volume of fluid queried in flow cell 100 is 0.4 ul, giving perhaps 300 unique readings/mm in a standard 14 mm diameter gradient, where bands of particles are between 1 and 4 mm tall. By expanding the Z-axis to a 2 mm square or circular light path, the volume of the flow path queried is now 8 ul, still allowing 18 readings/mm and increasing the light 20-fold. When absorbance and fluorescence are both to be detected, whatever light pipe geometry is chosen, it will be important to keep the cross section in all 4 light pipes (112) the same so that the same volume of the flow path is queried with each light pulse.

Figure 3B:
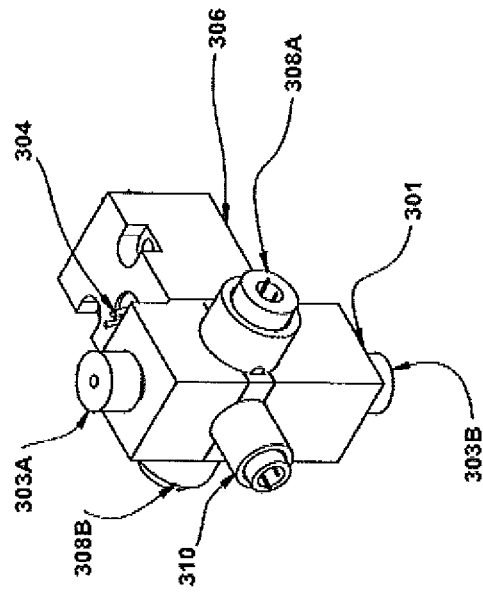
FIG. 3B is a perspective view of an assembled apparatus incorporating the flow cell of FIG. 1, according to an embodiment of the present application.
Figure 3A:
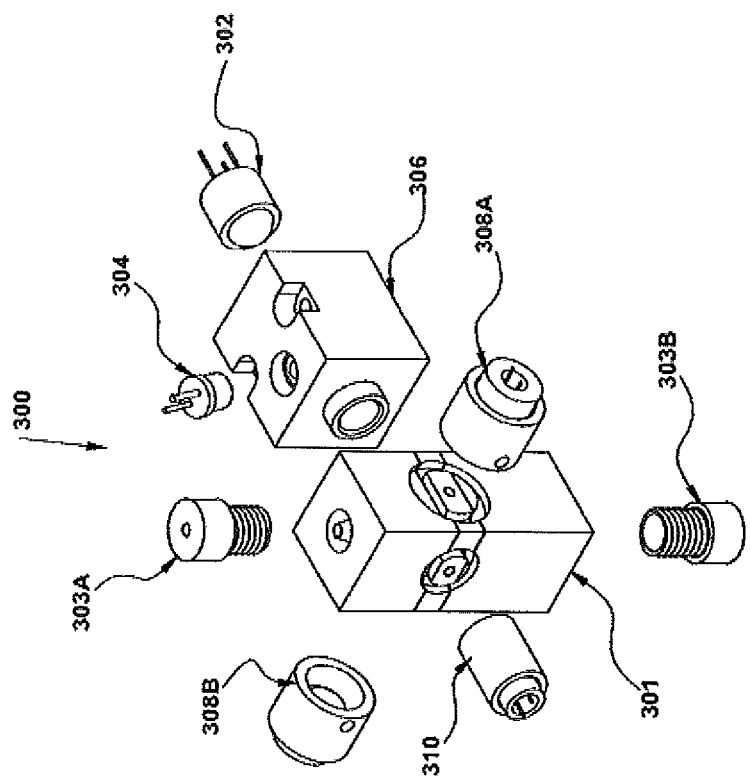
FIG. 3A is an exploded view of an apparatus incorporating the flow cell of FIG. 1, according to an embodiment of the present application.
Figure 3C:
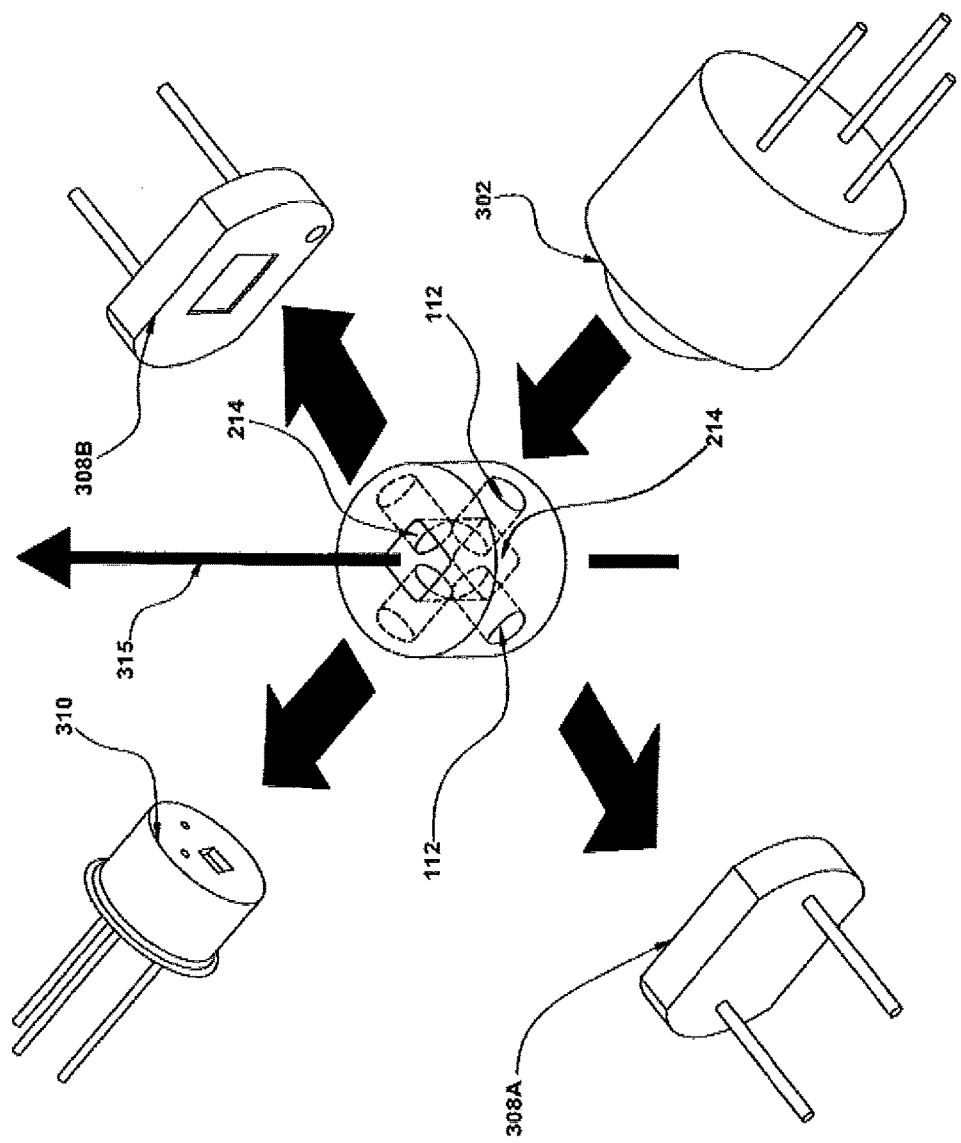
FIG. 3C is an exploded view of the central section of the flow cell of FIG. 1 showing its connections to the light source(s), and absorbance/fluorescence photodiodes, according to an embodiment of the present application.
Figure 3D:
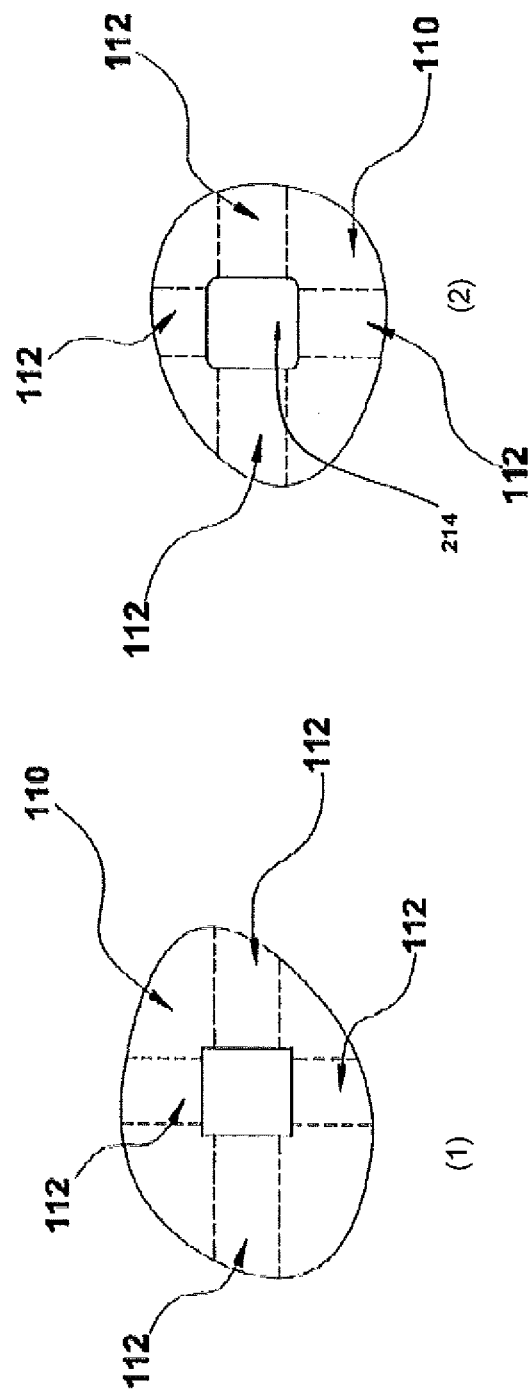
FIG. 3D is a cross section of the central section showing the rounded corners that eliminate the trapping of liquid that results with the sharp corners of a regular square cross-section.

While many sizes of the flow cell are suitable, the flow cell exemplified in one embodiment of the present application comprises a square fluid path 105 with radiused corners, e.g. a fluid path 105 sized 2×2 mm (0.079") with 0.010" radiused corners (as in FIG. 3D(2)) rather than the square corners (as in FIG. 3D(1)). The flowing liquid typically enters the flow cell at the bottom of the fluid flow section 109, carried there by Teflon™ tubing with a 0.025" bore, and exits the flow cell at the top of the fluid flow section 109 in the same diameter Teflon™ tubing. Consequently, the fluid path 105 goes from the tubing's 0.025" diameter to a rounded 0.079" square cross section of the central core chamber and back to the 0.025" diameter of the outlet tubing. The present flow cell 100 provides a tapered input and a tapered output where the bottom funnel 108 and the top funnel 106 of the fluid path 105 each have a cone portion 202, 206 for a portion (e.g. half) of their lengths. In the other portion of the funnel, the cone shape is gradually distorted into the rounded corner square shape of the core chamber 214 via cone-to-square conversion portions 204, 208.

The flow cell 100 with a core chamber 214 having a cross section of a 2×2 mm square provides a strong signal in both absorbance and fluorescence. However, the sharp corners of a square chamber retard the liquid flow in the corners, causing mixing of the central fluid with the "older" retarded fluid. Accordingly, the flow cell 100 of the present application provides rounded corners (FIG. 3D(2)) in the core chamber 214 to prevent trapping of liquid in the core chamber 214. In an exemplary embodiment, the corners are rounded to a 0.010" radius, which prevents trapping of the liquid.

It is important to note that liquid flowing in narrow bore tubing is subject to laminar capillary flow. The central lamina is the fastest moving liquid, and the liquid at the tubing wall, called the boundary layer, is immobile, with a gradient of laminar speeds between the wall and the central core of the tubing. In any flow cell design where narrow bore tubing carries the liquid to and from the flow cell, the flow is expanded to an appropriate size for absorbance and fluorescence detection in a manner that reduces both laminar capillary flow and turbulence. This is particularly important when the liquid flow is a gradient of a viscous, dense solution such as sucrose or glycerol, and therefore it is important for density gradient fractionation. If the central lamina is denser and more viscous than the outlying lamina surrounding it, any turbulence in the flow as the liquid passes through the core chamber 214 creates refractive index mixing lines, called Schlieren lines, that radically disturb the transmission of light across the flow cell, introducing noise in the signal. While the gradual transition of the fluid path 105 within the bottom funnel 108 from the cone portion 206 to the cone-to-square conversion portion 208 does not eliminate the laminar nature of the flow, it does reduce the turbulence and noise of such flow. The moving body of liquid maintains contact with the wall as it expands, entering the flow cell chamber 214 as a body with little or no mixing of fresh fluid with older fluid. Without this gradual transition, a core of fresh liquid passes more quickly through the middle of the flow cell, with gradual, turbulent mixing with older liquid that flows outside the central lamina.

Figure 10A:
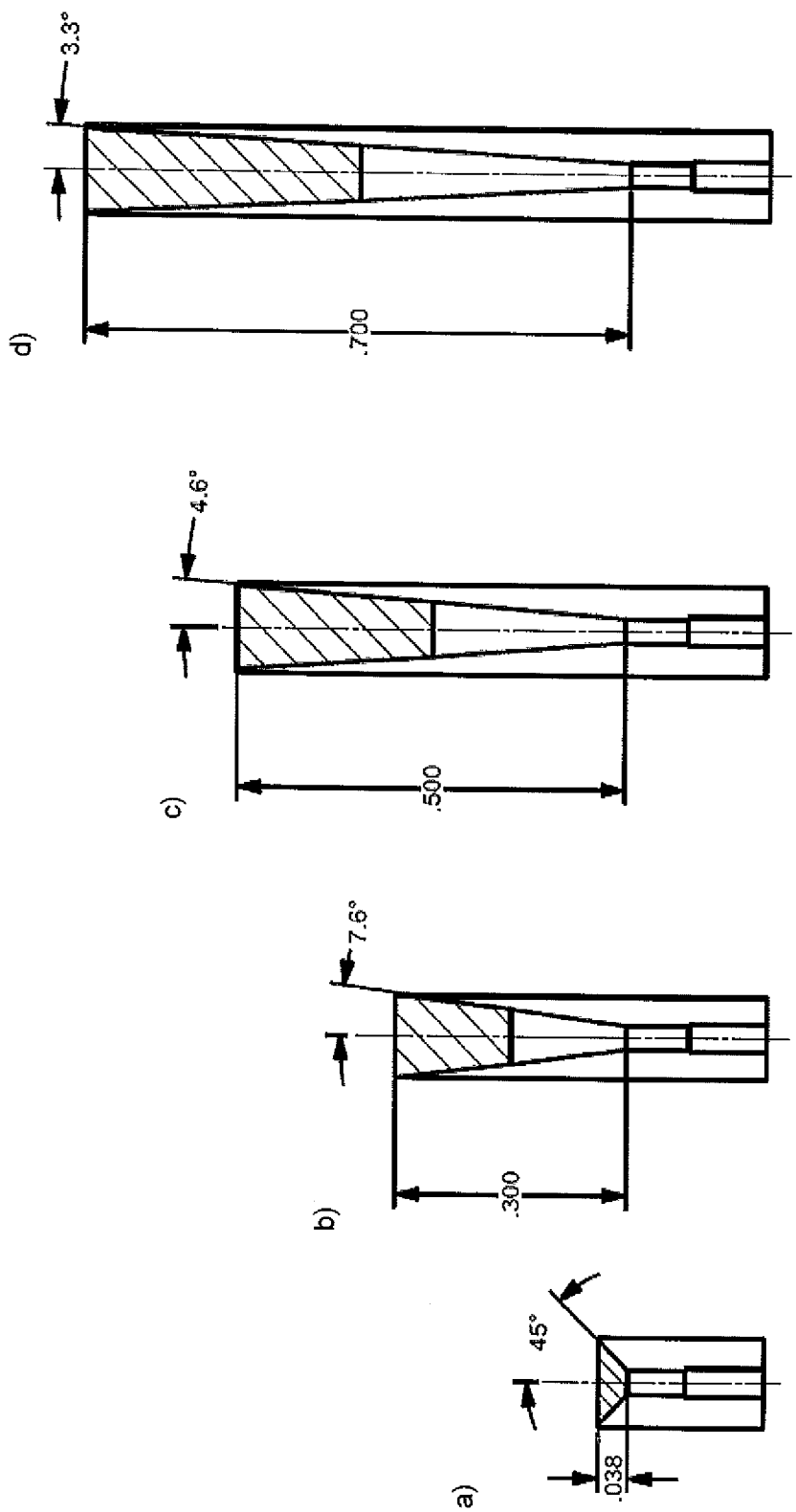
FIG. 10A is a cross section view of bottom funnels of the flow cell of various lengths.

Flow cell tests were conducted to illustrate the relation between flow velocity, funnel length and the decoupling of the flow from the wall. Funnels of various lengths from 0.3"-0.7" were tested. As shown in FIG. 10A, in each example, the narrow diameter is the size of fluid flowing into the flow cell exiting the tubing (e.g. 0.025") and the large dimension at the opposite end (e.g. 0.103") is the diagonal distance of the recess in the core chamber. As shown: a) is a funnel having the standard 45° angle cone found in typical flow cell designs where the flow area is expanded to adapt to the size of the flow cell; b) is a funnel with a total length of 0.3"; c) is a funnel with a total length of 0.5"; and d) is a funnel with a total length of 0.7". There is a decrease in the funnel angle with increasing funnel length. These cone angles from 7.6° to 3.3° are a fraction of the 45° funnels found in most, if not all, other designs. In the present design, each funnel is split into two halves, with the bottom half a pure cone and the top half a cone to square transition.

Figure 10B:
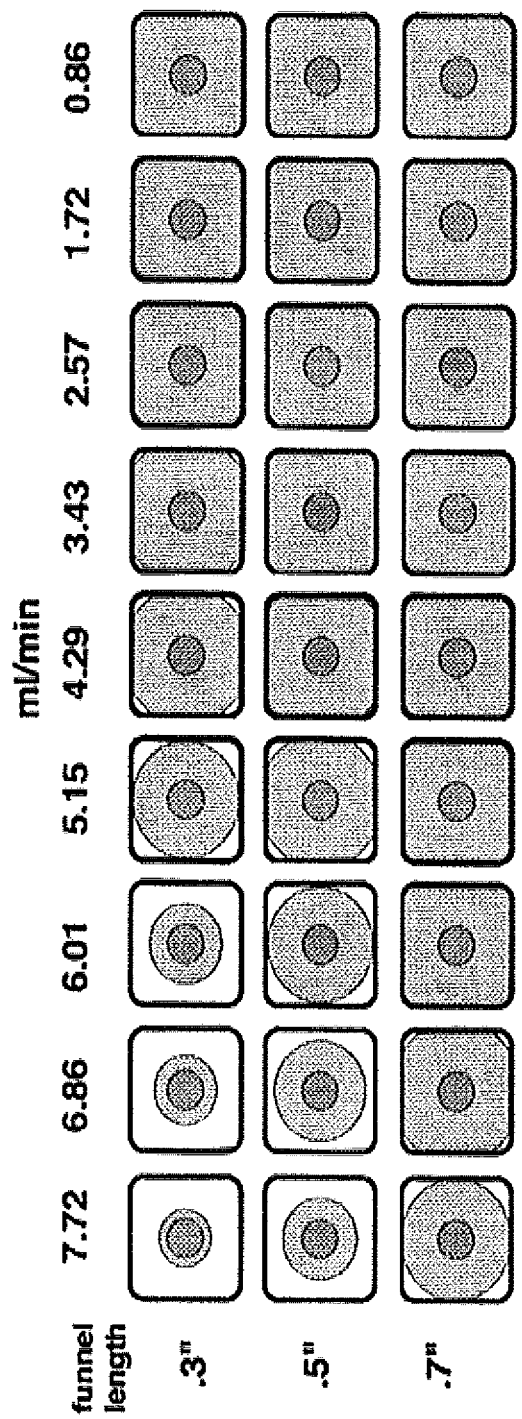
FIG. 10B is the view looking down from the top of the funnels of FIG. 10A at different flow rates, showing the spread of the incoming flow through the funnels.

The effect of flow rate and funnel length on the spreading of the flow is demonstrated in FIG. 10B, where the small circle in the center of each square is the size of fluid flowing into the flow cell from the teflon tubing (e.g. 0.025") and the large dimension at the opposite end (e.g. 0.103") is the diagonal distance of the recess in the core chamber.

In FIG. 10B, blue dyed water was injected into the narrow end of the funnels in FIG. 10A (*b*)-(*d*) at nine (9) different flow rates between 7.7 to 0.86 ml/min, The flowing dye was recorded on video, and the width of the blue dye was measured across the diagonal at the open end. FIG. 10B shows the width of the flow at these different flow rates and lengths of funnel. The view is looking down the funnel from its wide upper end showing the diameter of the flow as it leaves the funnel and enters the core chamber. The small central circle represents the diameter of the input tubing's inner bore (in an example embodiment, 0.025") and the shaded circle around it shows the area covered by the blue dyed flow as it leaves the top of the funnel and enters the core chamber 214 represented by the rounded square, which in some embodiments has the same dimensions as the top of each of the funnels.

To illustrate the extremes of this test, it is observed that the top left (in an example test configuration of a 0.3" funnel at 7.72 ml/min) has a thin shaft of blue dye in the core chamber completely detached from the wall over its entire length, while the bottom right square (in an example test configuration of a 0.7" funnel at 0.86 ml/min) shows that the dyed liquid remains in complete contact with the wall of the core chamber. At flow rates below 2 ml/min, all three funnel lengths have shallow enough cone angles to allow the flow to adhere to the wall over the entire length of the funnel. As the flow rate increases, however, the flow begins to detach from the wall in the 0.3" and 0.5" funnels. The 0.7" funnel keeps the flow against the wall at flow rates up to 6 ml/min. At 8 ml/min, all three funnel lengths show virtually complete separation of the flow from the wall. Thus, the longer the funnel length, the smaller the cone angle of the funnel, the greater the flow rate can be without detachment of the flow from the wall of the core chamber. The result is clear: keeping the flow smooth, turbulence-free and against the funnel's wall for any given flow rate can be accomplished using a funnel of the appropriate length and cone angle.

FIG. 10C is a graph of the same data shown in FIG. 10B.

To summarize, there is a clear correlation between the flow rate and the tendency of the central lamina to pull away from the wall of the funnel, creating undesirable turbulent flow and mixing within the flow cell. At high flow rates with the shorter funnel lengths, the central lamina can be seen with dye as a thin cylinder racing through the center of the flow cell, completely disengaged from the wall. With the longer funnel length, 0.7", this tendency is greatly reduced. Thus, the length of the bottom funnel is adapted to the flow rate to reduce the laminar flow effect. In an exemplary embodiment, the total length of the bottom funnel 108 is 0.400", or a length resulting in a funnel angle (from narrow to wide end) of less than about 10°, and in some embodiments less than about 7°, for example, less than 6', less than 5° or less than 4°. Having the bottom funnel 108 with this total length, keeps the liquid in contact with the wall of the bottom funnel 108 as it expands from the input tubing to the 2×2 mm cross sectional dimension of the core chamber 214, thus preventing detachment of the flow from the wall. This minimizes the turbulence within the flow cell and the noise this would add to both absorbance and fluorescence measurements.

Virtually all conventional flow cells with changing diameters within the fluid path use very short cones with an angle of 45° to spread fluid flow and then concentrate the flow. As shown in FIG. 10A, the largest funnel angle tested had a 7.6° taper and it showed significant detachment of the flow at flow rates above 2.5 ml/min. A 45° cone that is ⅒ as long as the 7.6° funnel can only avoid detachment at extremely low flow rates. Flow rates seen in chromatography and gradient fractionation would cause the solution entering the cone's bottom to form a narrow cylinder detached from the wall, causing turbulence and mixing.

In another embodiment, noise reduction in the present invention may be further achieved by the incorporation of flat ends on the light pipes 112 (e.g. fused silica light pipes) which are then flush to the smooth walls of the central chamber. The flat ends may, for example, be polished to optimize a flush fit. On each of the four internal faces of the central chamber, the light pipes occupy the center of the flat surfaces between the ends of the radiused corners shown in FIG. 3D(2), eliminating the light pipes as a source of turbulence. FIG. 3D(2) is a cross section of the core chamber 214 showing the rounded corners that eliminate the trapping of liquid that result with the sharp corners of a regular square shape. Having the light pipes 112 flush to the walls of the core chamber 214 prevents turbulence in the flow The four light pipes 112 as in the present design permit approximately 80% of the flowing liquid (e.g. 1.6 mm light pipes in a 2 mm flow cell cross section) to be queried in both the X- and Y-axis directions. The queried volume passing through the light path in the flow cell 100 allows for a stronger signal to be generated from the same volume of liquid, while avoiding the retention of liquid in the sharp corners.

Thus, the shape of the flow cell is shown to have an impact on its performance. The gradual taper of the funnels as the flow enters and departs the core chamber 214 of the central section. The smooth, rounded inner surfaces of the core chamber provide the least turbulence and mixing of the flow, preserving the separation of particles achieved in the column or gradient for downstream analysis and preventing refractive index Schlieren mixing lines found in density gradient eluents, and the background noise such mixing will cause. During analysis of density gradients used in centrifugal separation of particles, the concentration of the solute is constantly changing in the flow cell, producing changes in the refractive index of the flowing liquid. For example, in a 12 ml, 5-50% sucrose gradient at a flow rate of 2 ml/min, the concentration of sucrose is changing at 0.13%/sec. Thus, any turbulence causing chaotic mixing will produce Schlieren lines in the flow and radically increase the background noise in the light passing through the flow.

Another benefit of the streamline flow path is the elimination of bubbles that frequently remain in the flow cell during a run, obscuring the light beam, and at worst ruining the scan of an experiment altogether. When the flow cell of the current embodiment is dried between runs (e.g. tests), the arrival of the first liquid leaves the central chamber of the flow cell consistently bubble-free so that the flow cell software can use the sudden change on absorbance as the start signal for recording the run. In some embodiments, the flow cell is rinsed between runs.

The modular design of the flow cell 100 allows for a variety of simultaneous measurements, for example: (1) with one wavelength of input light, either UV absorbance or fluorescence can be measured. If the particle of interest both absorbs and fluoresces from this incident wavelength, both measurements can simultaneously be recorded. (2) With two wavelengths of input light, simultaneous measurements, such as: (a) one UV absorbance measurement and one fluorescence measurement; (b) two UV absorbance measurements; and (c) two fluorescence measurements are possible, and (3) with three wavelengths of light, simultaneous measurements, such as (a) one UV absorbance measurement and two fluorescence measurements; and (b) two UV absorbance measurements and one fluorescence measurement are enabled.

For example, the flow cell apparatus 300 illustrated in FIGS. 3A and 3B has a single light input and provides, for example, one UV absorbance measurement (e.g. at 260 or 280 nm) or one visible light absorbance measurement, as well as measurement of emitted fluorescence. FIG. 3A illustrates a flow cell apparatus 300, incorporating the flow cell design of FIG. 1, according to an embodiment of the present application. Particularly, the apparatus 300 comprises a single LED light source 302 (e.g. 1 UV or 1 VIS wavelength), an absorbance photodiode (PD) 310 and two fluorescence photodiodes (PD) 308A, 308B for measuring absorbance and fluorescence, respectively. In FIG. 3A, the light source 302, which may be an LED, is contained in the input holder 306. If needed, a filter (not shown) can also be installed in the input holder 306 for filtering the wavelengths of the light from the LED light source 302. For example, a narrow bandpass filter could reduce the range of wavelengths entering the flow cell from the LED if the LED's spectral output overlaps the emission of the fluor in use.

The input holder 306 further includes a reference photodiode (PD) 304. As shown in FIG. 3, the pins of the reference PD 304 protrude from the top of the input holder 306. In an exemplary embodiment, the reference (or normalizing) PD 304 is positioned at a 75° angle relative to the light beam such that the reference PD 304 captures the requisite amount of stray light without blocking the light beam that is focussed on the light pipe 112 by the hemispherical ball lens of the LED light source 302. This reference PD 304 permits normalization of the incident LED beam for drift and electronic noise by aiming the reference PD 304 at an oblique angle to the beam of the light source 302. FIG. 4 is a plan view 400 of the input holder 306 for a single input light source, and shows the reference PD 304 angled relative, to the light beam to normalize the intensity and drift of the light source.

The light source 302 and photodiodes 310 and 308 are connected to the flow cell (FIG. 3C) and emit and receive light through light pipes 112 (e.g. solid fused silica light pipes) in the walls of the flow cell as previously described, in communication with the core chamber 214 of the fluid flow section of the flow cell. The absorbance photodiode (PD) 310 is on the opposing side of the flow cell 300 relative to the input holder 306. Two fluorescent photodiodes (PD) 308A, 308B are perpendicular to the absorbance PD 310. The absorbance PD 310 measures the absorbance of the particles in a flowing liquid.

In some embodiments, the liquid flows into the fluid flow section in the direction 315 (Z-axis) shown in FIG. 3C. Absorbance is measured in the flow cell apparatus 300 by exposing light from the light source 302 to the flowing liquid in the fluid flow section and measuring absorbance in a straight path to the absorbance PD 310. Fluorescence is measured in the flow cell apparatus 300 by photodiodes 308A/B, which measure the light emitted by the particles in the flowing liquid in the fluid flow section (FIGS. 3B and 3C) at right angles to the incident beam from the light source 302. Accordingly, the flow cell apparatus 300 simultaneously monitors and measures the absorbance and fluorescence of particles in the flowing liquid. Particularly, the core chamber 214 is a hollow space through which the liquid flows. The core chamber 214 of the fluid flow section 109 may be made from a plastic material, for example Delrin®. The flow cell center section 110 has four cavities for receiving light pipes 112 and these cavities extend from the external surface of the flow cell center section 110 to the walls of the core chamber 214 (FIGS. 1 and 2). When the light pipes 112 are inserted into the cavities of the flow cell center section 110 (as shown in FIG. 1), the inner end of the light pipes 112 are flush with the walls of the core chamber 214 such that the liquid flowing through the core chamber 214 is not disturbed by the light pipes 112. At the points on the core chamber 214 that align with the inner ends of the light pipes 112, the core chamber 214 has four "windows" or openings which permit transmission of light into or out of the core chamber 214. As previously discussed, the light pipes 112 permit transmission of input light from the light source 302 into the flowing liquid in the fluid flow section 109, and permit absorbed and emitted light to be detected by the photodetectors. For example, the four windows may be round and may be made of quartz (fused silica). While it is often difficult to source plastic optical fibers (POF) of the same diameter as the quartz rods, where visible light is being transmitted, there may be reasons to use POF rods instead of quartz ones. The first window of the core chamber 214 receives the incident beam from the light source 302 containing UV and/or visible wavelengths. A second window opposing the first window receives absorbed light from the flowing liquid. Third and fourth opposing windows are on the emission output face sides of the flow cell 300, and perpendicular to the first and second windows, and they receive fluorescent emission at one or more particular wavelengths.

A benefit of using light pipes 112 in the present flow cell is that they provide flexibility, e.g. the ability to easily plug into different light sources (e.g. LEDs, Xenon lamps, lasers, fiber optic light bundles carrying multiple wavelengths) when and where needed. The present flow cell device is thereby modular and suitable for many different kinds of measurements.

In another embodiment, the windows in the walls of the core chamber 214 may be covered with glass or quartz for separating the light source from the liquid in the flow cell. For example, the cover may be a disc made of glass or quartz that seals the openings in the wall of the core chamber 214. As well, a light source such as a small LED mounted on a tiny SMT chip may be mounted behind the glass or quartz windows of the two opposing openings in the center section 110. Similarly, small photodiodes mounted on a tiny SMT chip may be mounted behind the glass or quartz window of the other two opposing openings in the center section 110. In this embodiment, the central components (e.g. light source, photodiodes) of the flow cell are small dedicated chips fixed in place in the openings of the core chamber 214, which saves space in the overall size of the flow cell.

In use, a solution flows through the fluid flow section 109 in the direction (315) shown in FIG. 3C. Particles of interest within the flowing solution, such as microbes, proteins or nanotubes, are detected by absorbance PD 310 when they absorb light from the beam of light from the light source(s) 302 having a desired excitation wavelength. The particles of interest within the flowing solution may also emit light at a different wavelengths, e.g. an emission wavelength, which may be detected by the fluorescence PDs 308A, 308B.

Thus, light travels in one direction emitted from the light source 302 into the flowing fluid in the chamber and absorption of this light is detected by the absorbance photodiode 310 which is situated opposite to the light source. Emitted light within the chamber travels away from the central core to the fluorescent opposing PDs 308A, 308B which are in a path perpendicular to the path of the light source/absorbance PD.

Figure 5B:
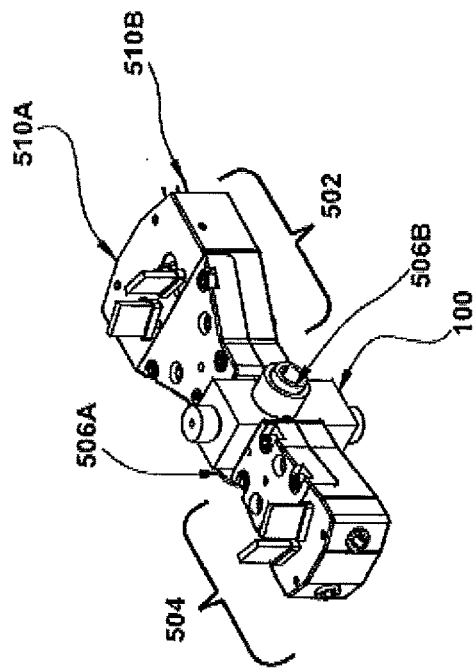
FIG. 5B is a perspective view of the assembled apparatus of FIG. 5A according to a second embodiment of the present application.
Figure 5A:
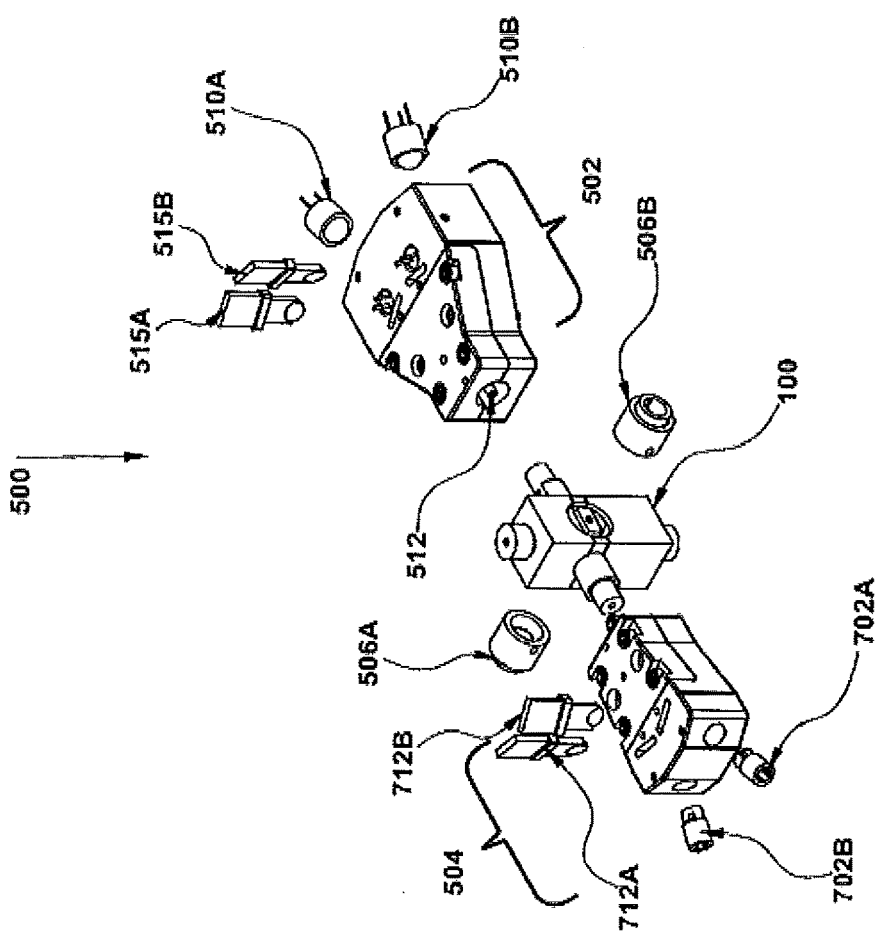
FIG. 5A is an exploded view of an apparatus incorporating the flow cell of FIG. 1 and having a two (dual) input module and a two (dual) output module, according to a second embodiment of the present application.

FIG. 5A is an exploded view and FIG. 5B is a perspective view of a flow cell apparatus 500 incorporating the flow cell 100 of FIG. 1 and having two light inputs and two light outputs, as well as two photodiodes for fluorescence measurement, thereby facilitating two simultaneous light absorption measurements and fluorescence emission, according to a second embodiment of the present application. The flow cell apparatus 500 may permit two UV absorbance measurements, one UV absorbance measurement and one visible light measurement or two visible light wavelengths, as well as one or two emission wavelengths.

With the flow cell apparatus 500, one or more different wavelengths of excitation light may be transmitted into the central chamber 214 through the light input face using appropriate light sources, fiber optic bundles and/or light filters.

As well, with the flow cell apparatus 500, one or more different wavelengths of absorbed light may be measured independently and simultaneously at the absorbance output face of the light pipe located directly across from the input light face. In one embodiment, a single absorption wavelength is measured by a photodiode at the absorption output face. In another embodiment, the absorbance light can be divided into separate fiber bundles leading to differentially filtered photodiodes, so that two or more absorbance wavelengths can be monitored from the single absorbance output face.

Also, with the flow cell apparatus 500, one or more different wavelengths of emitted light may be independently and simultaneously measured at both of the emission output faces of the light pipes located at right angles to the input light face. In one embodiment, a single emission wavelength is measured at each of the two emission output faces. In another embodiment, the fluorescence emission at each output face can be divided into separate fiber bundles leading to differentially filtered photodiodes, so that two or more fluorescent wavelengths could be monitored at each of the two emission output faces.

Figure 6B:
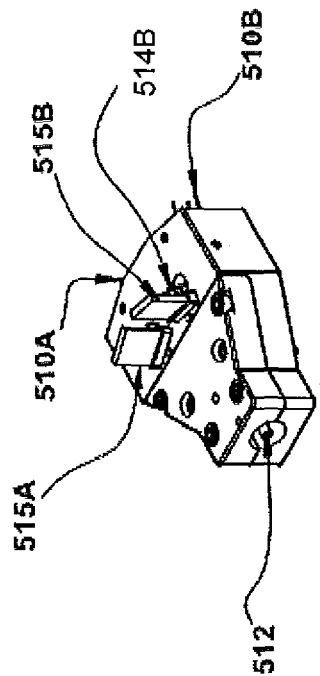
FIG. 6B is a perspective view of the assembled two (dual) input module of the apparatus of FIG. 5A, according to the second embodiment of the present application.
Figure 6A:
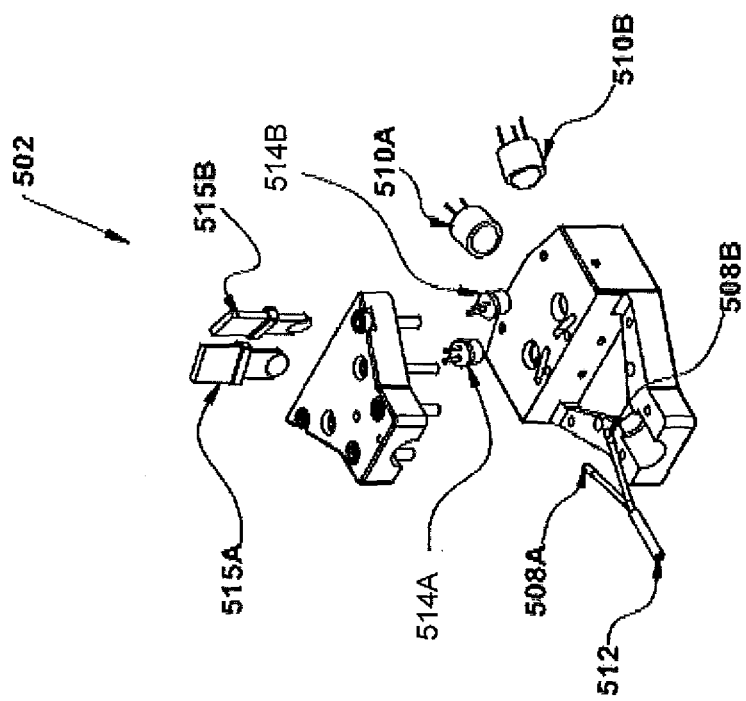
FIG. 6A is an exploded view of the two (dual) input module of the apparatus of FIG. 5A, according to the second embodiment of the present application.
Figure 6C:
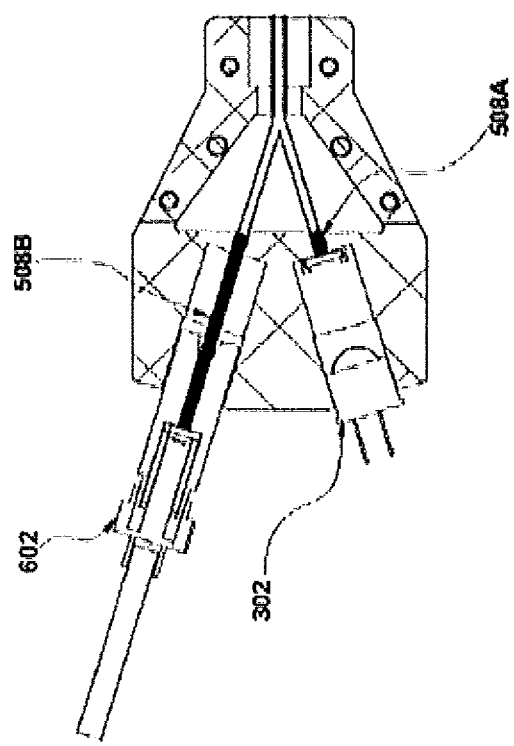
FIG. 6C is a side cut-away view of the assembled two (dual) input module of the apparatus of FIG. 5A, according to the second embodiment of the present application.

In another exemplary embodiment, FIG. 6C, the second light source 602 can be a xenon lamp triggered to fire at the same time as the LED (PX2, Ocean Optics, Dunedin Fla., USA). The xenon beam covers the spectrum from the UV to the IR, offering great flexibility in the choice of fluorescent excitation applications. Further enhancing this range is the availability of dual bandpass filters which permit the probing of two different fluors such as Green Fluorescent Protein (GFP) and mCherry in the same burst of light (Chroma Technology Corp, VT, USA). The two fluorescence PDs 506A and 506B at right angles to the incident beam would have different filters, each passing the emission of the designated fluor. Alternatively, the light source 602 in FIG. 6C can be a laser, of which there are dozens of different wavelengths available (e.g. Changchun New Industries Optoelectronics Technology Co. Ltd., China).

The dual wavelength apparatus shown in FIG. 5A/B comprises the flow cell 100, a dual light input module 502 and a dual light output module 504. As shown in FIG. 5B, the flow cell 100 is located in the middle of apparatus 500 and the input module 502 and the output module 504 are located on opposite sides of the flow cell 100. The two light sources 510A, 510B focus their light on the light pipe ends 508A and 508B of light pipe 512 (FIG. 6A) on the input face of the flow cell 100. Two fluorescence photodiodes 506A, 506B are positioned on the emission output faces of the flow cell 100 and perpendicular to the input module 502 and the output module 504.

FIG. 6A is an exploded view, FIG. 6B is an enlarged perspective view and FIG. 6C is a top view of the dual light input module 502 of the apparatus 500 of FIG. 5, according to the second embodiment of the present application. The dual light input module 502 may receive as inputs, two UV wavelengths (e.g. 2 UV), one UV wavelength and one visible light wavelength (e.g. 1 UV and 1 VIS) or two visible light wavelengths (e.g. 2 VIS). As shown in FIG. 6, the two input light sources 510A, 510B (e.g. LEDs) each focus their light beams on bifurcated fiber optic bundles (e.g. separate input arms) 508A/B. The separate input arms of the fiber optic bundles 508A, 508B meet and the light they carry is mixed in a single fiber bundle 512, providing even illumination to the fiber optic light pipe 512 (e.g. quartz light rod) that carries the light beam into the flow cell's 100 core chamber. The input light sources 510A, 510B may be light emitting diodes (LEDs) emitting in a selected wavelength range for detection of UV-absorbing particles. In alternative embodiments, the suitable light sources may be LEDs emitting in the visible range. As well, in some embodiments the dual light input module 502 includes filters 515A, 515B, such as bandpass filters, that may filter the light emitted from the two input light sources 510A, 510B, respectively. This allows the input light beam to be further modified, if necessary. For example, the filters 515A, 515B may filter and separate the various wavelengths of light aimed at the flowing liquid. Different wavelengths may be required depending on the application and the type of liquid in the flow cell. Further, in some embodiments the dual light input module 502 further includes reference (e.g. normalizing) PDs 514A, 514B that are positioned at a 75° relative to the light beam such that the reference PDs 514A, 514B capture the requisite light without blocking the light beam that is focussed on the fiber optic bundles 508A, 508B.

In some embodiments, there may be multiple fluorescence outputs at each emission output face. For example, bifurcated light pipes and trifurcated light pipes may be used as the emission output faces of the flow cell 100 to allow multiple fluorescence outputs at each emission output face.

Figure 7B:
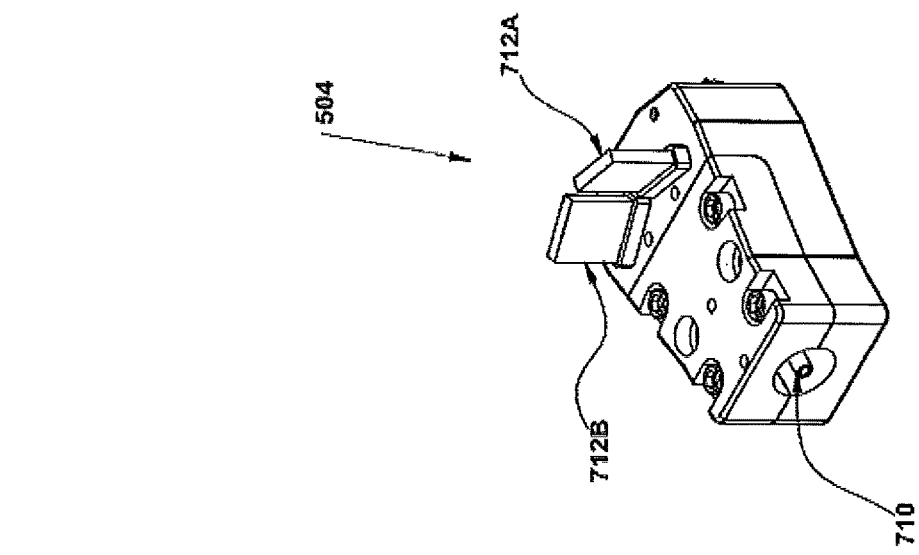
FIG. 7B is a perspective view of the assembled two (dual) output module of the apparatus of FIG. 5A, according to the second embodiment of the present application.
Figure 7A:
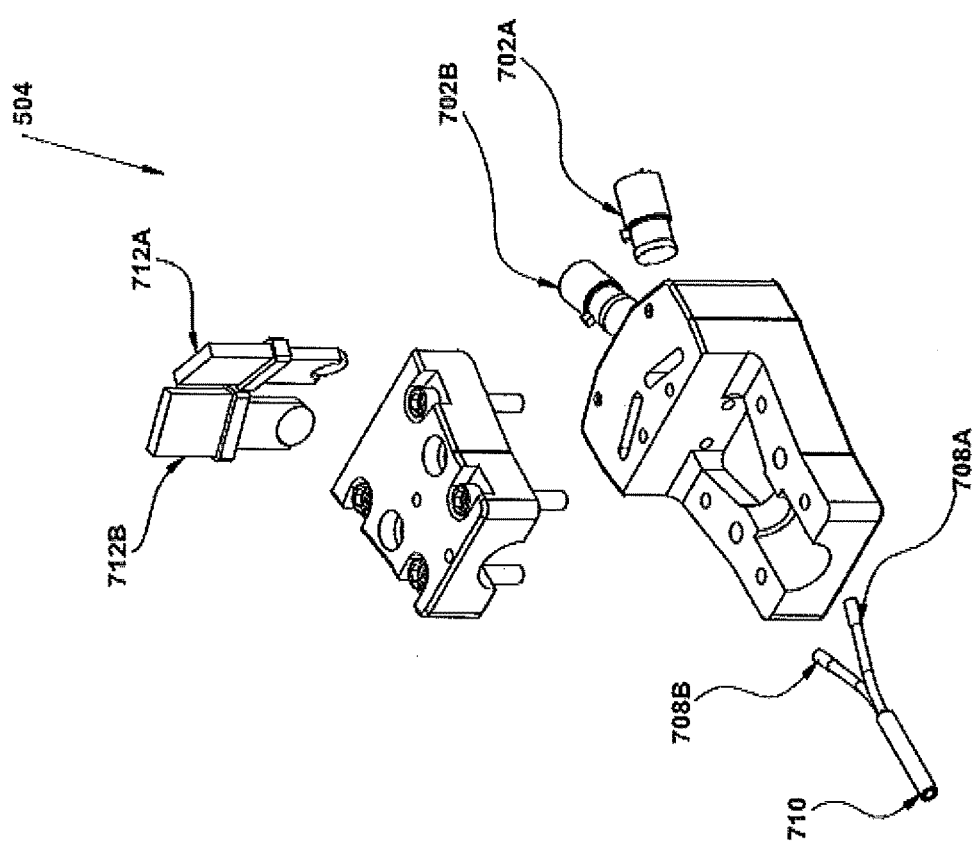
FIG. 7A is an exploded view of the two (dual) output module of the apparatus of FIG. 5A, according to the second embodiment of the present application.

FIG. 7A is an exploded view and FIG. 7B is an enlarged perspective view of the dual output module 504 of the apparatus 500 of FIG. 5, according to the second embodiment of the present application. The dual output module 504 includes a fiber optic light pipe 710, bifurcated fiber optic bundles 708A, 708B and two absorbance PDs 702A, 702B. As well, in some embodiments, the dual output module 504 may include filters 712A, 712B, such as bandpass filters, that are used to filter the light from the bifurcated light fiber bundles 708A, 708B such that the two absorbance PDs 702A, 702B receive the filtered light. The addition of the filters 712A, 712B allows the absorbed light to be further modified, if necessary. For example, the filters 712A, 712B may filter and separate the various wavelengths of light received as absorbed light from the flowing liquid in the flow cell.

FIG. 8A is an exploded view and FIG. 8B is an enlarged perspective view of a three input module 800 for use with a flow cell 100, according to a third embodiment of the present application. The three input module 800 of the may receive as inputs three UV wavelengths (e.g. 3 UV), three visible light wavelengths (e.g. 3 VIS), two UV wavelengths and one visible light wavelength or vice versa (e.g. 2 UV and 1 VIS or 1 UV and 2 VIS). As shown in FIG. 8, there are three input light sources 802A, 802B, 802C (e.g. LEDs), each of which focus their light beams on trifurcated fiber optic bundles (e.g. separate input arms) 808A, 808B, 808C that join with the combined fiber optic light pipe 810. The separate input arms of the fiber optic bundles 808A, 808B, 808C meet and the light they carry is mixed in the single bundle 810, so that they provide even illumination to the fiber optic light pipe 112 (e.g. quartz light rod) that carries the light beam into the flow cell's 214 central core. The input light sources 802A, 802B, 802C may be light emitting diodes (LEDs) emitting in a selected wavelength range for detection of UV-absorbing particles. In alternative embodiments, the suitable light sources may be LEDs emitting in the visible range. As well, in some embodiments the three input module 800 includes filters 812A, 812B, 812C, one for each light source. The filters 812A, 812B, 812C may be bandpass filters that filter the light emitted from the three input light sources 802A, 802B, 802C respectively. This allows the input light beam to be further modified if necessary. For example, the filters 812A, 812B, 812C may filter and separate the various wavelengths of light aimed at the flowing liquid. Different wavelengths may be required depending on the application and the type of liquid in the flow cell. Due to the modular design of the flow cell and related apparatuses of the present application, the three input module 800 may replace the single input module 306 in FIG. 3, thereby having the three input module 800 being used with the flow cell, single output absorbance PD and the two fluorescence PDs shown in FIG. 3. Further, in some embodiments the three input module 800 further includes reference (e.g. normalizing) PDs 814A, 814B, 814C that are positioned at a 75° relative to the light beam such that the reference PDs 814A, 814B, 814C captures the requisite light without blocking the light beam that is focussed on the fiber optic bundles 808A, 808B, 808C.

As one of skill will appreciate, for flow cell apparatuses that comprise two or more light sources, they may additionally comprise electronic means for simultaneously pulsing the light sources, as well as means to simultaneously record the absorbance and fluorescence output of the photodiodes receiving light absorbance or emission. In an example embodiment, the Burr-Brown microprocessor (now Texas Instruments DDC118IRTCT) offers 1-8 channels to measure the output of the various photodiodes described herein.

As one of skill in the art will appreciate, for example, the fiber optic bundles 508A, 508B, 708A, 708B, 808A, 808B, 808C and the fiber optic light pipe 512, 710 and 810 will incorporate fibers manufactured of material appropriate for the transmission of the wave-length of the light emitted from the light source(s). For example, if the light sources emit in the UV range from 250 to 350 nm, quartz (fused silica) fibers may be used. Plastic optical fibers (POF) are used to carry visible light. The number and diameter of the fibers in the fiber optic bundles is optimized empirically to provide the highest signal to noise ratio and the highest resolution in a given application. For example, in certain embodiments, such as those illustrated in FIGS. 6, 7 and 8, total of 30 fibers with 0.1 mm diameter are found in the common fiber bundle 510 at the base of the branches. In some embodiments, a total of 33 fibers with 0.2 mm diameter are found in the common fiber bundle 510 at the base of the branches.

In use, the light emitted from one or more light sources within a flow cell apparatus according to the application travels from the input module through the flowing liquid in the core chamber of the fluid flow section of the flow cell to the output module for detection by the absorbance photodiode(s). In addition, emitted fluorescence may be detected by the fluorescence PDs in the present flow cell apparatus. The fluorescence PDs may detect particles by their natural fluorescence, by the enhanced fluorescence of a wide variety of commercial dyes that bind specifically to biological molecules of interest or by fluorescent dye-tagged antibodies. For example, viruses can be detected using a DNA-binding dye called PicoGreen™ (Molecular Probes, Invitrogen, USA) (for example, see "Quantitation of Adenovirus DNA and Virus Particles with the PicoGreen Fluorescent Dye, Murakami P.; McCaman M. T. Analytical Biochemistry, Volume 274, Number 2, October 1999, pp. 283-288"). The excitation light source for PicoGreen™ delivered would be at 485 nm and the emission wavelength received would be 538 or 518 nm. These dyes offer sensitivity that is reportedly 10,000 times more sensitive than UV absorbance. A series of fluorescent dyes (CF™ dyes from Biotium™, USA, <www.biotium.com>) have been coupled to antibodies for ultrasensitive detection of target proteins in larger macromolecular assemblies and cells.

In conventional UV monitors, there is typically a range of Absorbance Units Full Scale (AUFS) settings from 2 to 0.01 AUFS. The absorbance is represented in units of OD (optical density), with the appropriate (AUFS) range selected before the scan is obtained. The UV monitor has a fixed analog voltage output, typically 0-1.0 VDC, which represents the range of OD in the selected AUFS. For example, a voltage output of 0.5 VDC at an AUFS setting of 0.05 gives an OD of 0.025. However, if the user sets the range at 0.2 AUFS and the OD of the sample exceeds 0.2 OD, the voltage output flatlines at 1.0 V, 0.2 OD, and the excess OD is not recorded. A further issue with these UV monitors is that voltages below 0 cannot be recorded. If the instrument is zeroed in water and its "zero reading" drifts higher, the actual sample can have less absorbance than the zeroing solution, and the OD will flatline at 0.00 OD.

With the flow cell of the present application, there is no AUFS setting. Using, for example, a built-in Analog to Digital Burr-Brown microprocessor with a resolution of 1 part/1,044,175 (or approximately 1 part/1,040,000 parts), any peak, large or small, is recorded with the same high resolution. The flow cell is calibrated with a water blank and a known standard with an OD between 2 and 3, and in some embodiments an OD as high as 4.5. The flow cell has consistently shown linearity from 0 to 4.5 OD, where most other conventional flow cells offer linearity only as high as 2.0. During use, the OD of the flowing liquid is calculated with a linear response between the blank and the standard. However, the extraordinarily large dynamic range of the Burr-Brown microprocessor allows the extension of the range of detectable optical densities to be as high as 35 OD. These high ODs are no longer linear with increasing absorbance, but the measured data shows consistent and measureable declines in light transmission at these extraordinarily high optical densities. With a large dynamic range of absorbance readings there is no need to preset the AUFS before starting a recording. When the data is graphed, appropriate curve fitting algorithms may be used to calculate the approximate OD at these high levels.

On the low end of the OD scale, if the blank solution used to zero the device has residual OD and the sample transmits more light than the zero standard, the OD is reported as a negative value, but the offset is easily corrected and the run is not lost.

The flow cell apparatuses of the present invention may be housed within a user interface device. For example, the user interface device in addition to the flow cell apparatus may further include a circuit board for receiving the simultaneous output of absorbance and fluorescence measurements from the flow cell apparatus. Particularly, the pins of the absorbance PD and the fluorescence PD in the flow cell apparatus may be received into the circuit board by means of a suitable temporary shielded connector. The user interface device may include one or more processors or microprocessors, such as a central processing unit (CPU), connected to the circuit board. The CPU performs arithmetic calculations and control functions for the circuit board and/or flow cell apparatus, including processing the current measurements from the absorbance PDs and fluorescence PDs and may further convert them into digital values. The processor (e.g. CPU) may also run software programs and applications for controlling and programming the flow cell apparatus. As well, the user interface device may include a display screen, such as a liquid display screen (LCD) that displays the measured data from the absorbance photodiodes and fluorescence photodiodes. Also, the user interface device may include an internal memory, such as random access memory (RAM) and/or read only memory (ROM), and possibly additional memory, for storing the measured data from the flow cell apparatus and storing and running software and software applications. The user interface device may further include a power source and/or power connector, an input/output communications system for interfacing with other computers, computer systems and wireless networks, and input devices such as keyboards, buttons, and switches.

As well, the digitized measurements from the flow cell apparatuses of FIGS. 3 and 6, may be transmitted to and received by any suitable computer or microprocessor-based system, such as a desktop or laptop computer or a mobile wireless telecommunication computing device, such as a smartphone or tablet computer. The computer or microprocessor-based system may be coupled to the user interface device and/or circuit board containing the flow cell apparatus via a wired or wireless connection. The measured data from the flow cell apparatus may be processed on the user interface device or may be transmitted to the computer or microprocessor-based system for processing over a wired or wireless network connection such as the Internet. An illustrative computer system may include a display, input devices in the form of keyboard and pointing device, computer and external devices.

The computer may contain one or more processors or microprocessors, such as a central processing unit (CPU). The CPU performs arithmetic calculations and control functions to execute software stored in an internal memory, preferably random access memory (RAM) and/or read only memory (ROM), and possibly additional memory. The additional memory may include, for example, mass memory storage, hard disk drives, optical disk drives (including CD and DVD drives), magnetic disk drives, magnetic tape drives (including LTO, DLT, DAT and DCC), flash drives, program cartridges and cartridge interfaces, removable memory chips such as EPROM or PROM, emerging storage media, such as holographic storage, or similar storage media as known in the art. This additional memory may be physically internal to the computer, external, or both. The computer system may also include other similar means for allowing computer programs or other instructions to be loaded. Such means can include, for example, a communications interface which allows software and data to be transferred between the computer system and external systems and networks. Examples of communications interface include a modem, a network interface such as an Ethernet card, a wireless communication interface, or a serial or parallel communications port. Software and data transferred via communications interface are in the form of signals which can be electronic, acoustic, electromagnetic, optical or other signals capable of being received by communications interface. Multiple interfaces, of course, may be provided on a single computer system.

Input and output to and from the computer is administered by the input/output (I/O) interface. This I/O interface administers control of the display, keyboard, external devices and other such components of the computer system. The computer will generally include a graphical processing unit (GPU) useful for computational purposes as an adjunct to, or instead of, the CPU, for mathematical calculations.

The various components of the computer system are coupled to one another either directly or by coupling to suitable buses.

The flow cell designs of the present invention require no rinsing to remove bubbles from the fluid flow section of the flow cell after a first liquid has flowed through. For example, the meniscus of a liquid going through a rinsed and dried flow cell drives out all the bubbles in the fluid flow section of the flow cell. As such, the measuring of a flowing liquid may start instantly. The change in optical density (OD) is detected as the meniscus flows through the fluid flow section of the flow cell, for example, by software in communication with the circuit board connected to the photodiodes.

The flow cell 100 and flow cell apparatuses of the present application are compatible with a variety of light sources, e.g. any optical application of any wavelength of light from 200 nm-1300 nm, including ultraviolet, visible and near infrared. For example, in an exemplary embodiment shown in FIG. 1, a xenon light source, such as the Ocean Optics™ PX2 xenon light source, may be used and directed to the flow cell with a light pipe and adaptor 900. In such an embodiment, the broad spectrum of incoming light may be filtered down to specific wavelengths by a Chroma™ dual bandpass filter. The filtered excitation wavelengths may then enter the flow cell coupled with a UV pulse at 260 nm. The UV beam intensity is measured by the absorbance photodiode positioned directly opposite the incoming light beam, while any fluorescent emissions generated by the two input excitation wavelengths are measured separately by two photodiodes positioned at right angles to the incoming beam, each of which is filtered down to receive only one of the two possible emission wavelengths.

In a further embodiment, a photodiode array (not shown) may be used to sample the entire light spectrum for absorbance and/or fluorescence with single pulses from a light source such as the xenon light source.

In a further embodiment, the light source may be a laser of the desired wavelength connected to the dual input apparatus, as shown for the xenon source in FIG. 6C

Although the disclosure describes and illustrates the preferred embodiments of the invention, it is understood that the invention is not limited to these particular embodiments. Many variations and modifications will occur to those skilled in the art. For definition of the invention, reference is made to the appended claims.

The invention claimed is:

1. A flow cell comprising:
a housing configured to contain the internal components of the flow cell having a light input face, an absorbance output face and first and second emission output faces;
a fluid flow section within the housing that comprises a bottom funnel through which fluid enters the flow cell, a core chamber into which fluid flows from the bottom funnel, and a top funnel into which fluid flows from the core chamber, wherein the bottom and top funnels each comprise a first end which extends at an angle to a second end that is wider in diameter than the first end, and said second end of each is adjacent to and aligned with the core chamber, wherein the core chamber has a square cross-sectional shape with rounded corners; and
a center section within the housing center having a recess formed therein which houses the core chamber of the fluid flow section, wherein said center section comprises a first pair of opposing channels formed in the light input face and the absorbance output face, respectively, and a second pair of opposing channels formed in the first emission output face and the second emission output face and which are perpendicular to the first pair of opposing channels, and wherein the first pair of opposing channels and second pair of opposing channels are in communication with the core chamber.

2. The flow cell of claim 1, wherein the bottom and top funnel each comprise a cone portion that transitions into a cone-to-square conversion portion, wherein the cone-to-square conversion portion of each is aligned with the core chamber.

3. The flow cell of claim 2, wherein the cone portion and the cone-to-square conversion portion are of equal length.

4. The flow cell of claim 2, wherein the angle from the first end to the second end of the bottom funnel is less than 10°.

5. The flow cell of claim 2, wherein the bottom and top funnels comprise a length and funnel angle that prevents decoupling of a central lamina of fluid flowing through the core chamber.

6. The flow cell of claim 1, further comprising light pipes in each of the first pair of opposing channels and the second pair of opposing channels.

7. The flow cell of claim 6, wherein the light pipes are made of quartz or plastic optical fibers.

8. The flow cell of claim 7, wherein the light pipes illuminate about 80% of a liquid path in the core chamber.

9. The flow cell of claim 6, wherein the light pipes are flush with the walls of the core chamber.

10. The flow cell of claim 1, wherein in the first pair of opposing channels, one channel comprises a light source and the opposing channel comprises at least one photodiode to detect light absorbance.

11. The flow cell of claim 1, wherein in the second pair of opposing channels, each channel comprises at least one photodiode to detect fluorescence.

12. A flow cell apparatus comprising:
a flow cell as defined in claim 1;
one or more light sources at the light input face of the flow cell housing for directing light into liquid in the core chamber of the flow cell through the channel at the light input face;
one or more absorbance photodiodes at the absorbance output face of the flow cell housing for measuring light absorbance within the liquid in the core chamber of the flow cell through the channel at the absorbance output face; and
fluorescence photodiodes at each of the first and second emission output faces of the flow cell housing for measuring fluorescence within liquid in the core chamber of the flow cell through the channels at the first and second emission output faces.

13. The flow cell apparatus of claim 12, comprising one or more light sources which emit different wavelengths of excitation light into the core chamber.

14. The flow cell apparatus of claim 12, comprising differentially filtered absorbance photodiodes that independently and simultaneously measure light absorbance at different wavelengths.

15. The flow cell apparatus of claim 12, wherein a single emission wavelength is measured at each of the two emission output faces.

16. The flow cell apparatus of claim 12, wherein the fluorescence emission is detected at each emission output face by differentially filtered photodiodes, so that two or more fluorescent wavelengths independently and simultaneously measured at each of the two emission output faces.

17. The flow cell apparatus of claim 12, wherein the light source transmits light which is received by the absorbance photodiode.

18. The flow cell apparatus of claim 12, wherein each of the fluorescence photodiodes absorb light emitted from the center of the core chamber.

* * * * *